(12) United States Patent
Han

(10) Patent No.: US 8,871,749 B2
(45) Date of Patent: Oct. 28, 2014

(54) BONE-TRANSPLANT OR BONE-FILLING COMPOSITION COMPRISING A DIHYDROXYBENZOIC ACID DERIVATIVE

(75) Inventor: Jae-Jin Han, Yongin-si (KR)

(73) Assignee: Cellsafe Co., Ltd., Gyeonggi-do (KR)

( * ) Notice: Subject to any disclaimer, the term of this patent is extended or adjusted under 35 U.S.C. 154(b) by 0 days.

(21) Appl. No.: 13/643,803

(22) PCT Filed: Apr. 25, 2011

(86) PCT No.: PCT/KR2011/002975
§ 371 (c)(1),
(2), (4) Date: Nov. 6, 2012

(87) PCT Pub. No.: WO2011/136513
PCT Pub. Date: Nov. 3, 2011

(65) Prior Publication Data
US 2013/0053354 A1    Feb. 28, 2013

(30) Foreign Application Priority Data
Apr. 29, 2010    (KR) .......................... 10-2010-0039829

(51) Int. Cl.
| | | |
|---|---|---|
| A61K 31/60 | (2006.01) | |
| A61K 31/235 | (2006.01) | |
| A61K 31/618 | (2006.01) | |
| A61L 27/50 | (2006.01) | |
| C07C 69/84 | (2006.01) | |
| A61C 8/02 | (2006.01) | |
| C07C 65/03 | (2006.01) | |

(52) U.S. Cl.
CPC .......... *A61C 8/0006* (2013.01); *A61L 2430/02* (2013.01); *A61L 27/50* (2013.01); *A61L 2430/12* (2013.01); *C07C 69/84* (2013.01); *C07C 65/03* (2013.01)

USPC ........................ 514/159; 514/544; 514/618

(58) Field of Classification Search
USPC .......................................... 514/159, 544, 568
See application file for complete search history.

(56) References Cited

U.S. PATENT DOCUMENTS

| | | | |
|---|---|---|---|
| 2002/0132875 A1 | 9/2002 | Stadtmueller | |
| 2005/0238683 A1 | 10/2005 | Adhikari et al. | |
| 2005/0287085 A1 | 12/2005 | Cazor et al. | |
| 2006/0115514 A1 | 6/2006 | Gengrinovitch | |
| 2007/0071790 A1 | 3/2007 | Ameer et al. | |
| 2008/0167513 A1 | 7/2008 | Hansen et al. | |
| 2010/0015164 A1* | 1/2010 | Clemens et al. ........... | 424/178.1 |
| 2010/0129417 A1 | 5/2010 | Moses et al. | |

FOREIGN PATENT DOCUMENTS

| | | |
|---|---|---|
| KR | 10-2009-0069063 A | 6/2009 |
| WO | 2008/137807 A1 | 11/2008 |
| WO | 2008/157177 A1 | 12/2008 |

OTHER PUBLICATIONS

Welch, et al., "Effect of Recombinant Human Bone Morphogenetic Protein-2 on Fracture Healing in a Goat Tibial Fracture Model", Journal of Bone and Mineral Research, vol. 13, No. 9, pp. 1483-1490, (1998).
Yasko, et al., "The Healing of Segmental Bone Defects, Induced by Recombinant Human Bone Morphogenetic Protein (rhBMP-2)", The Journal of Bone and Joint Surgery, Incorporated, vol. 74-A, No. 5, pp. 659-670, (1992).
Supplementary European Search Report, two pages, completed on Dec. 10, 2013.

* cited by examiner

*Primary Examiner* — Zohreh Fay
(74) *Attorney, Agent, or Firm* — Vorys, Sater, Seymour and Pease LLP; Mihsun Koh

(57) ABSTRACT

Provided is a bone-transplant or bone-filling composition, which comprises a dihydroxybenzoic acid derivative which has been newly demonstrated to increase the activity of osteoblasts and so induce bone formation.

5 Claims, No Drawings

BONE-TRANSPLANT OR BONE-FILLING COMPOSITION COMPRISING A DIHYDROXYBENZOIC ACID DERIVATIVE

TECHNICAL FIELD

The present invention relates to a bone-grafting or bone-filling composition comprising a dihydroxybenzoic acid derivative. It is newly found by the present invention that the dihydroxybenzoic acid derivative increases an activity of osteoblasts, thereby inducing bone formation.

BACKGROUND ART

Teeth and bones are a sole hard tissue in the body. Loss or defect in teeth and bones, which often occurs from fracture due to e.g., car accidents, results in morphological changes and/or functional disorder. In order to regenerate bone defect, there are being used various bone-grafting or bone-filling methods, using allograft, xenograft, metallic materials, polymer materials, ceramics, etc.

Materials supplementing the site of bone defects (conventionally, referred to as "bone-fillers") are used for carrying out the bone-grafting or bone-filling methods. Recently, in order to reform legs for height-increase or reform dwarf jaws, osteogenesis is frequently performed, which results in increasing demand for bone-fillers.

Bio-materials incorporated into the human body as a bone-filler or a bone-grafting material may be classified into a bioinert material, a bioactive material, and a biodegradable material. The bio-inert material refers to a material neither inducing inflammation and toxicity nor binding to a biological tissue, when applied to a human body. The bioactive material refers to a material having high biocompatibility, which makes it possible to biochemically bind to adjacent tissues, when applied to a human body. The biodegradable material refers to a material absorbed or degraded in the body, after graft thereof. And also, the bio-materials may be classified into a metallic material, a ceramic material (i.e., an inorganic material), and a polymer material, according to a law material. The metallic material and the ceramic material are used mainly as a substitute for hard tissue such as teeth and bones. Recently, in order to utilize advantages of each material, a complex of ceramic and polymer or a mixture of metal and ceramic is occasionally used.

Metals have higher mechanical strength than ceramics and polymers. Stainless steel, an alloy of cobalt (Co) and chromium (Cr), titanium (Ti), titanium alloy (Ti-6Al-4V), a metallic mixture of titanium and nickel (1:1, atom ratio), etc. are used for a bone-filler or a bone-grafting material. Although metals are used mainly in a fine form, they are used in a porous metal form or in a metallic fiber form coated on a substrate surface, according to necessity. When metals in a porous metal form are grafted into a body, bone may be grown into the pores (small holes) of the substitute, which gives stronger binding between the bone and the substitute. And, metals or metallic fibers coated or adsorbed on a substitute surface provides concavo-convex forms on the surface, thereby enabling bone to grow into the gap, which gives high mechanical fixing effects.

Ceramic materials (i.e., inorganic materials) can provide superior chemical binding to bone, because the inorganic component of bones and teeth, i.e., apatite, is a ceramic material. Alumina and zirconia having good mechanical properties are used for bone-terminal and artificial tooth-root that require enduring abrasion. Bioactive ceramic materials include bioactive glasses having calcium oxide (CaO) and silicon dioxide ($SiO_2$) as a main ingredient, and calcium phosphate ceramics having calcium and phosphorus that are major component of bone. Crystallized glasses of sodium oxide ($Na_2O$)-calcium oxide-silicon dioxide are bioactive and have improved mechanical strengths such as flexural strength, fracture toughness, fatigue life, etc. Therefore, they are used for artificial spine, artificial ilium (hip bone), etc. Tricalcium phosphate ($Ca_3(PO_4)_2$, TCP), composed of calcium and phosphorus similarly to apatite, has a continuously absorbed property, when grafted into a body. Therefore, it is widely used as a substitute material of hard tissues in the fields of orthopedics and orthodontics. Bioactive ceramics are appropriately used as bone fillers packing defected tooth or bones in a lump form. For this purpose, porous apatite, a complex of apatite and tricalcium phosphate, and a bioactive glass are mainly used as bone fillers. They are prepared conventionally in a 3-5 mm granular form, which is packed into defected sites of a bone. Bioactive ceramics may be used alone; be coated on metal surface for overcoming disadvantages of a metal substitute; or be used as injectable bone cements that fix a substitute by being injected in a cement form. The coating a metal substitute with bioactive ceramics can inhibit dissolution of metallic ions and also provide direct binding between the metal substitute and an adjacent bone without forming a fibrous coating layer. Currently, artificial hip joints coated with apatite or apatite and TCT are commercially available. And also, metallic screws or pins coated with bioactive ceramics are being introduced to markets.

Polymer materials include polylactic acid (PLA) or its copolymers and biodegradable polymers such as collagen. The polymer materials may be used for reducing modulus of elasticity, through mixing with metals or nonmetals (e.g., apatite).

Bone-grafting and bone-filling materials include an autologous bone, an allogeneic bone, a xenogenic bone, and said synthetic bones prepared with various bio materials. Among them, synthetic bones are mainly used, considering potential infection risk and economic issue. Hydroxyapatite is conventionally used as a main material of synthetic bones. Although hydroxyapatite has excellent osteoconductivity, it has low osteoinductivity. Therefore, when applied to a body, hydroxyapatite shows large deviation in bone-forming periods, according to patients' states and ages.

In order to overcome such disadvantages of synthetic bones, BMPs (bone morphogenic proteins) or other bone-grafting substitutes are used for inducing bone regeneration. For example, it has been reported that BMP2 facilitates fracture healing in a fracture-induced animal study (Welch, R. D. et al., J Bone Miner Res. 13(9):1483-1490, 1998; Yasko, A. W. et al., J Bone Joint Surg. 74A:659-671, 1992). On the basis of such research results, BMP2 was approved by the US FDA and is being used as a fracture-treating agent, a bone-grafting material, and a bone-filler, through applying to collagen sponge and various scaffolds. However, BMPs are very expensive and require using a large amount thereof. Therefore, because of high cost, the utilization of these proteins for bone-grafting or bone filling is limited.

DISCLOSURE

Technical Problem

The present inventor has performed various researches for finding materials activating osteoblasts, thereby inducing bone formation, the materials of which can be usefully applied to a bone-grafting or bone-filling composition. Especially, the present inventor designs various derivatives from herb (Rubus coreanus Miquel)-derived compounds and then evaluated their inducing activities of bone formation. As a result thereof, the present inventor surprisingly found that dihydroxybenzoic acid derivatives, especially dihydroxybenzoic acid derivatives substituted with hydroxy groups at 2,4-positions or 2,5-positions of benzoic acid, remarkably increase alkaline phosphatase activity, calcium accumulation, and alveolar bone formation.

Therefore, the present invention provides a bone-grafting or bone-filling composition comprising dihydroxybenzoic acid derivatives.

Technical Solution

In accordance with an aspect of the present invention, there is provided a bone-grafting or bone-filling composition, which comprises at least one dihydroxybenzoic acid derivatives selected from the group consisting of 2,3-dihydroxybenzoic acid, 2,4-dihydroxybenzoic acid, 2,5-dihydroxybenzoic acid, ethyl 3,4-dihydroxybenzoate, 3,5-dihydroxybenzoic acid, ethyl 2,4-dihydroxybenzoate, methyl 2,4-dihydroxybenzoate, ethyl 2,5-dihydroxybenzoate, ethyl 2,6-dihydroxybenzoate, and ethyl 3,5-dihydroxybenzoate.

In the bone-grafting or bone-filling composition, the dihydroxybenzoic acid derivative may be preferably ethyl 3,4-dihydroxybenzoate, ethyl 2,4-dihydroxybenzoate, or ethyl 2,5-dihydroxybenzoate, more preferably ethyl 2,4-dihydroxybenzoate or ethyl 2,5-dihydroxybenzoate. The bone-grafting or bone-filling composition may be in a form of artificial bone, artificial joint, bone cement, or bone substitute. And also, the bone-grafting or bone-filling composition may be in a form of artificial tooth, periodontal tissue regenerate, tooth regenerate, or dental implant, more preferably in a form of dental implant.

Advantageous Effects

It is newly found by the present invention that dihydroxybenzoic acid derivatives can facilitate osteoblast activation required for bone formation, fracture healing and tooth growth and development, thereby usefully applying to a bone-grafting or bone-filling composition. In particular, ethyl 2,4-dihydroxybenzoate and ethyl 2,5-dihydroxybenzoate showed remarkably increased alkaline phosphatase activity, calcium accumulation, and alveolar bone formation. Accordingly, the dihydroxybenzoic acid derivatives, including 2,4-dihydroxybenzoate and ethyl 2,5-dihydroxybenzoate, can be usefully used for orthopedic bone-grafting and bone filling in forms of artificial bone, artificial joint, bone cement, bone substitute, or bone regenerate; and for orthodontic bone-grafting and bone filling in forms of artificial tooth, periodontal tissue regenerate, tooth regenerate, or dental implant.

BEST MODE

The present invention provides a bone-grafting or bone-filling composition, which comprises at least one dihydroxybenzoic acid derivatives selected from the group consisting of 2,3-dihydroxybenzoic acid, 2,4-dihydroxybenzoic acid, 2,5-dihydroxybenzoic acid, ethyl 3,4-dihydroxybenzoate, 3,5-dihydroxybenzoic acid, ethyl 2,4-dihydroxybenzoate, methyl 2,4-dihydroxybenzoate, ethyl 2,5-dihydroxybenzoate, ethyl 2,6-dihydroxybenzoate, and ethyl 3,5-dihydroxybenzoate.

The present inventor designs various derivatives from Rubus coreanus Miquel-derived compounds and then evaluated their inducing activities of bone formation. In particular, the present inventor designs hydrolyzed forms in which their ester bonds are eliminated; and various derivatives having hydroxy substituents at different substitution sites, and then evaluated their inducing activities of bone formation. As a result thereof, the present inventor surprisingly found that various dihydroxybenzoic acid derivatives, especially dihydroxybenzoic acid derivatives substituted with hydroxy groups at 2,4-positions or 2,5-positions of benzoic acid, remarkably increase alkaline phosphatase activity, calcium accumulation, and alveolar bone formation. Accordingly, the dihydroxybenzoic acid derivatives, including 2,4-dihydroxybenzoate and ethyl 2,5-dihydroxybenzoate, can be economically and usefully used for orthopedic and orthodontic bone-grafting and bone filling composition.

Among the dihydroxybenzoic acid derivatives, ethyl 3,4-dihydroxybenzoate, ethyl 2,4-dihydroxybenzoate, and ethyl 2,5-dihydroxybenzoate are preferable. In particular, ethyl 2,4-dihydroxybenzoate (the compound of Formula 1), ethyl 2,5-dihydroxybenzoate (the compound of Formula 2), or its mixture are more preferable.

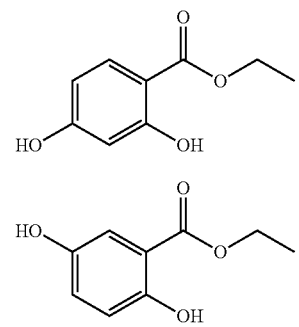

<Formula 1>

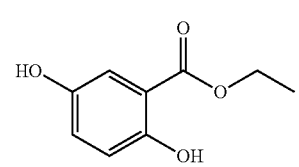

<Formula 2>

The composition of the present invention may be in an appropriate form for orthopedic use, i.e., a bone-grafting or bone-filling form conventionally used in patients suffering from fracture, etc. For example, the composition of the present invention may be in a form of artificial bone, artificial joint, bone cement, or bone substitute.

The artificial bone or the artificial joint may be prepared by coating the dihydroxybenzoic acid derivative on or mixing the dihydroxybenzoic acid derivative with a metal (such as titanium) or a nonmetal (such as hydroxyapatite, TCP (tricalcium phosphate) ceramics, bio glasses, carbon ceramics, alumina, etc.); and then molding the resulting product into an artificial bone form or an artificial joint form. And also, the artificial bone or the artificial joint may be prepared by coating the dihydroxybenzoic acid derivative on an artificial bone or an artificial joint molded with a metal or a nonmetal. The coating may be performed by dipping the metal or nonmetal in a solution of the dihydroxybenzoic acid derivative (for example, aqueous solution thereof) or spraying a solution of the dihydroxybenzoic acid derivative (for example, aqueous solution thereof) on the metal or nonmetal; and then drying the resulting product.

The bone cement may be prepared by coating the dihydroxybenzoic acid derivative on or mixing the dihydroxybenzoic acid derivative with a nonmetal (such as hydroxyapatite, TCP (tricalcium phosphate) ceramics, bio glasses, carbon ceramics, alumina, polymetamethylacrylate (PMMA), polylactic acid or its copolymer, etc.); and then molding the resulting product into a bone cement form. The coating may be performed by dipping the nonmetal in a solution of the dihydroxybenzoic acid derivative (for example, aqueous solution thereof) or spraying a solution of the dihydroxybenzoic acid derivative (for example, aqueous solution thereof) on the nonmetal; and then drying the resulting product.

The bone regenerate (also referred to as "bone substitute") may be prepared by coating the dihydroxybenzoic acid derivative on or mixing the dihydroxybenzoic acid derivative with a nonmetal (such as hydroxyapatite, TCP (tricalcium phosphate) ceramics, bio glasses, carbon ceramics, alumina, polymetamethylacrylate (PMMA), polylactic acid or its copolymer, etc.); and then molding the resulting product into a bone regenerate form. And also, the bone regenerate may be prepared by coating the dihydroxybenzoic acid derivative on a bone regenerate molded with a nonmetal. The coating may be performed by dipping the nonmetal in a solution of the dihydroxybenzoic acid derivative (for example, aqueous solution thereof) or spraying a solution of the dihydroxybenzoic acid derivative (for example, aqueous solution thereof) on the nonmetal; and then drying the resulting product.

In the bone-grafting or bone-filling composition for orthopedic use according the present invention, the dihydroxybenzoic acid derivative, preferably ethyl 3,4-dihydroxybenzoate, ethyl 2,4-dihydroxybenzoate or ethyl 2,5-dihydroxybenzoate, more preferably ethyl 2,4-dihydroxybenzoate or ethyl 2,5-dihydroxybenzoate may be present for example in an amount ranging from 1 mg/kg to 2000 mg/kg for adult use, the amount of which may be used in divided amounts (e.g., 1 to 3 times) according to necessity. The amount may vary according to patients' age, severeness, etc.

The composition of the present invention may be in an appropriate form for orthodontic use, i.e., a bone-grafting or bone-filling form conventionally used in patients suffering from tooth fracture, periodontal disease (e.g., loss of upper and lower alveolar bone), etc. For example, the composition of the present invention may be in a form of artificial tooth, periodontal tissue regenerate, tooth regenerate, or dental implant.

The artificial tooth or the dental implant may be prepared by coating the dihydroxybenzoic acid derivative on or mixing the dihydroxybenzoic acid derivative with a metal (such as titanium) or a nonmetal; and then molding the resulting product into an artificial tooth form or a dental implant form. And also, the artificial tooth or the dental implant may be prepared by coating the dihydroxybenzoic acid derivative on an artificial tooth or a dental implant molded with a metal or a nonmetal. The coating may be performed by dipping the metal or nonmetal in a solution of the dihydroxybenzoic acid derivative (for example, aqueous solution thereof) or spraying a solution of the dihydroxybenzoic acid derivative (for example, aqueous solution thereof) on the metal or nonmetal; and then drying the resulting product.

The periodontal tissue regenerate or the tooth regenerate may be prepared by coating the dihydroxybenzoic acid derivative on or mixing the dihydroxybenzoic acid derivative with a nonmetal (such as hydroxyapatite, TCP (tricalcium phosphate) ceramics, bio glasses, carbon ceramics, alumina, polymetamethylacrylate (PMMA), polylactic acid or its copolymer, etc.); and then molding the resulting product into a periodontal tissue regenerate form or a tooth regenerate form. The coating may be performed by dipping the nonmetal in a solution of the dihydroxybenzoic acid derivative (for example, aqueous solution thereof) or spraying a solution of the dihydroxybenzoic acid derivative (for example, aqueous solution thereof) on the nonmetal; and then drying the resulting product.

Preferably, the bone-grafting or bone-filling composition for orthodontic use according the present invention may be in a form of dental implant, comprising the dihydroxybenzoic acid derivative, preferably ethyl 3,4-dihydroxybenzoate, ethyl 2,4-dihydroxybenzoate or ethyl 2,5-dihydroxybenzoate, more preferably ethyl 2,4-dihydroxybenzoate or ethyl 2,5-dihydroxybenzoate. In the bone-grafting or bone-filling composition for orthodontic use according the present invention, the dihydroxybenzoic acid derivative may be present for example in an amount ranging from 1 mg/kg to 2000 mg/kg for adult use, the amount of which may be used in divided amounts (e.g., 1 to 3 times) according to necessity. The amount may vary according to patients' age, severeness, etc.

The present invention will be described in further detail with reference to the following examples. These examples are for illustrative purposes only and are not intended to limit the scope of the present invention.

Example 1

Compound Designs

Various derivatives including 3,4-dihydroxybenzoic acid ester were designed and their inducing activities of bone formation were evaluated. The derivatives include hydrolyzed forms in which their ester bonds are eliminated; and various derivatives having hydroxy substituents at different substitution sites. The chemical names and structures thereof are shown in the following table 1. The compounds shown in Table 1, all of which are known-compounds, were obtained from Sigma-Aldrich.

TABLE 1

| No. of Compd. | Chemical Name | Structure |
|---|---|---|
| NP21 | 2,3-dihydroxybenzoic acid | 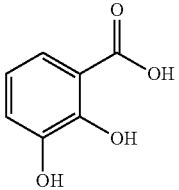 [SMILES: O=C(O)c1cccc(O)c1O] |
| NP22 | 2,4-dihydroxybenzoic acid | 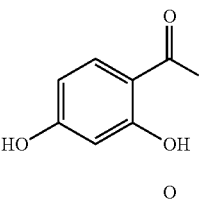 |
| NP23 | 2,5-dihydroxybenzoic acid | 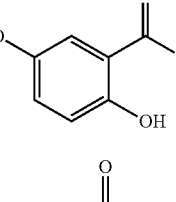 |
| NP31 | ethyl 3,4-dihydroxybenzoate | 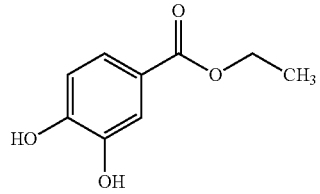 |

TABLE 1-continued

| No. of Compd. | Chemical Name | Structure |
|---|---|---|
| NP32 | 3,5-dihydroxybenzoic acid | 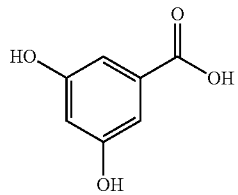 [SMILES: O=C(O)c1cc(O)cc(O)c1] |
| NP33 | ethyl 2,4-dihydroxybenzoate | 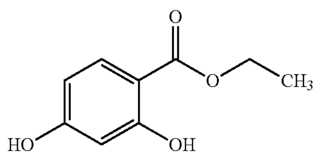 |
| NP34 | methyl 2,4-dihydroxybenzoate | 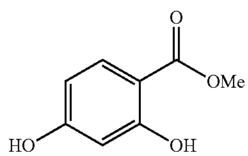 [SMILES: COC(=O)c1ccc(O)cc1O] |
| NP35 | ethyl 2,5-dihydroxybenzoate | 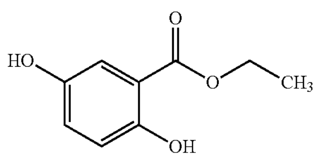 |
| NP36 | ethyl 2,6-dihydroxybenzoate | 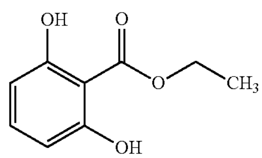 |
| NP37 | ethyl 3,5-dihydroxybenzoate | 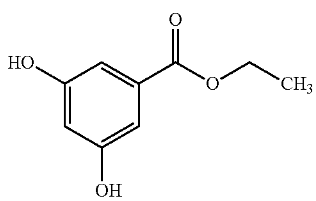 |

Example 2

Measurement of Alkaline Phosphatase (ALP) Activities

MC3T3-E1 cells (RIKEN Cell Bank, Japan) ($5 \times 10^3$ cells per well) as an osteoblast cell line were placed on each well of a 96-well plate and then cultured for 12 hours. After removing the medium, α-MEM supplemented with β-glycerophosphate and ascorbic acid were added thereto as a differentiation-inducing agent for osteoblasts. Each compound of Example 1 was added to the culture medium in the final concentration of 5 μg/ml. The plate containing the cells was cultured for 7 days. 100 μl of a cell lysis buffer (Sigma, Catalog number: MCL1) was added to the cells, which were then incubated at 37° C. for 30 minutes. The resulting mixture (50 μl) was reacted with p-nitrophenyl phosphate as a substrate in a 0.1N glycine-NaOH buffer (pH 9.8), at 37° C. for 30 minutes. Each amount of p-nitrophenol released from the substrate was quantified by measuring an absorbance at 405 nm using an ELISA reader (Bio-Tek instrument). A positive control was treated with BMP2 in the concentration of 100 ng/ml. The alkaline phosphatase activities were calculated by obtaining relative absorbance differences through comparing with a negative control (no treatment). The results thereof are shown in the following table 2.

TABLE 2

| No. of compound | Alkaline phosphatase activity of osteoblasts (%) |
|---|---|
| Negative control | 100 |
| Positive control (BMP2) | 150 |
| NP21 | 147 |
| NP22 | 153 |
| NP23 | 152 |
| NP31 | 200 |
| NP32 | 155 |
| NP33 | 430 |
| NP34 | 149 |
| NP35 | 560 |
| NP36 | 157 |
| NP37 | 153 |

From the results shown in Table 2, it can be seen that the dihydroxybenzoic acid derivatives designed in Example 1 showed excellent ALP activities. Especially, The compounds of NP33 and NP35, which have hydroxy groups at 2,4- and 2,5-position of benzoic acid respectively, showed most excellent ALP activities.

Example 3

Measurement of In-Vitro Bone Nodules of Osteoblasts

MC3T3-E1 cells (RIKEN Cell Bank, Japan) ($2 \times 10^3$ cells per well) as an osteoblast cell line were placed on each well of a 24-well plate and then cultured for 24 hours. The medium was changed with α-MEM supplemented with β-glycerophosphate and ascorbic acid as a differentiation-inducing agent for osteoblasts. Each compound of Example 1 was added to the culture medium in the final concentration of 5 μg/ml. The plate containing the cells was cultured for 27 days while changing the medium every three days or every four days. A positive control was treated with BMP2 in the concentration of 100 ng/ml. No treatment was made to the negative control. In order to quantify the amount of calcium accumulated in the cells, the cells were washed with a biological saline, and then calcium (Ca) was extracted with a 0.5N HCl solution for 6 hours on an agitator. The extracted solution (100 μl) was reacted with a Calcium Reagent (Sigma, USA) at room temperature for 5 minutes. An absorbance at 575 nm was measured with an ELISA reader (Bio-Tek instrument). The amount of calcium accumulated in the cells was calculated by obtaining relative absorbance differences through comparing with a negative control (no treatment). The results thereof are shown in the following table 3.

TABLE 3

| No. of compound | Calcium accumulation (%) |
|---|---|
| Negative control | 100 |
| Positive control (BMP2) | 160 |
| NP21 | 132 |
| NP22 | 159 |
| NP23 | 163 |

TABLE 3-continued

| No. of compound | Calcium accumulation (%) |
|---|---|
| NP31 | 180 |
| NP32 | 163 |
| NP33 | 420 |
| NP34 | 158 |
| NP35 | 580 |
| NP36 | 160 |
| NP37 | 159 |

From the results shown in Table 3, it can be seen that the dihydroxybenzoic acid derivatives designed in Example 1 showed excellent calcium accumulation in the cells. Especially, The compounds of NP33 and NP35, which have hydroxy groups at 2,4- and 2,5-position of benzoic acid respectively, showed most excellent calcium accumulation in the cells.

Example 4

Measurement of Alveolar Bone Formation Activity

Each compound of Example 1 was dissolved in a sterile biological saline to obtain a solution having a concentration of 1 mg/ml. Collagen bead (diameter: 1×2 mm, Gibco) used as a bone-grafting material was dipped into each solution at 37° C. for 45 minutes. Each resulting wet bead includes about 1-2 μl of the solution, and therefore 1-2 μg of each compound. Mandiblar molars before tooth-root formation were isolated from mice. The wet bead was inserted in the center of dental pulp of each isolated mandiblar molar, using tweezers. The resulting mandiblar molars were transplanted into the kidney of female mouse (C57BL/6). After 3 weeks, the growing molar teeth were fixed with a formalin solution and then stained with a Morse's solution. The stained sites were visualized under a microscope (Olympus IX71) and then the area was measured with an imageWarp software (London, England). The effects of the compounds on alveolar bone formation were evaluated by comparing with the negative control (100%). The results thereof are shown in the following table 4.

TABLE 4

| No. of compound | Alveolar bone formation (%) |
|---|---|
| Sterile biological saline | 100 |
| Positive control (BMP2) | 120 |
| NP21 | 110 |
| NP22 | 121 |
| NP23 | 119 |
| NP31 | 150 |
| NP32 | 123 |
| NP33 | 300 |
| NP34 | 130 |
| NP35 | 450 |
| NP36 | 121 |
| NP37 | 122 |

From the results shown in Table 4, it can be seen that the dihydroxybenzoic acid derivatives designed in Example 1 showed excellent alveolar bone formation activities. Especially, The compounds of NP33 and NP35, which have hydroxy groups at 2,4- and 2,5-position of benzoic acid respectively, showed most excellent alveolar bone formation activities.

Example 5

Cytotoxicity Test

In order to evaluate the cytotoxicities of the compounds designed in Example 1, L929 cells (RIKEN Cell Bank, Japan) ($1 \times 10^4$ cells per well) were placed on each well of a 96-well plate and then cultured for 12 hours. The cells were treated with each compound in predetermined concentrations and then cultured for 48 hours. After removing the medium, a MTT (3-(4,5-dimethylthiazol-2-yl)-2,5-diphenyltetrazolium bromide) solution (100 μl per well) was added to the cells, which were then incubated for 4 hours. After removing the supernatant, each well was treated with a DMSO solution (100 μl per well) and then incubated at room temperature for 10 minutes for extraction. An absorbance at 550 nm was measured with an ELISA reader (Bio-Tek instrument). The $CC_{50}$ (Cytotoxic Concentration 50%) values were determined by comparing with a negative control (no treatment). The results thereof are shown in the following table 5.

TABLE 5

| No. of compound | $CC_{50}$ (μg/ml) |
|---|---|
| DMSO | — |
| NP21 | 150 |
| NP22 | 150 |
| NP23 | 200 |
| NP31 | 100 |
| NP32 | 150 |
| NP33 | 100 |
| NP34 | 150 |
| NP35 | 150 |
| NP36 | 200 |
| NP37 | 150 |

From the results shown in Table 5, it can be seen that the dihydroxybenzoic acid derivatives designed in Example 1 have more than 100 μg/ml of $CC_{50}$ value, thereby showing relatively low cytotoxicity.

The invention claimed is:

1. A method of grafting or filling bone in a subject in need thereof comprising administering a bone-grating or bone-filling material to the subject, said material comprising an effective amount of ethyl 2,4-dihydroxybenzoate or ethyl 2,5-dihydroxybenzoate.

2. The method of claim 1, wherein the bone-grating or bone-filling material is in a form of artificial bone, artificial joint, bone cement, or bone substitute.

3. The method of claim 1, wherein the bone-grating or bone-filling material is in a form of artificial tooth, periodontal tissue regenerate, tooth regenerate, or dental implant.

4. The method of claim 3, wherein the bone-grating or bone-filling material is in a form of dental implant.

5. A method for increasing alkaline phosphatase activity or calcium accumulation in osteoblasts, or alveolar bone formation in a subject in need thereof comprising administering a bone-grating or bone-filling material to the subject, said material comprising an effective amount of ethyl 2,4-dihydroxybenzoate or ethyl 2,5-dihydroxybenzoate.

* * * * *